(12) United States Patent  
Borrye et al.

(10) Patent No.: US 9,486,595 B2  
(45) Date of Patent: Nov. 8, 2016

(54) TRACHEAL INTUBATION GUIDE

(75) Inventors: Steen Borrye, Hilleroed (DK); Merete Louise Borrye, Hilleroed (DE)

(73) Assignee: AMBU A/S, Ballerup (DK)

( * ) Notice: Subject to any disclaimer, the term of this patent is extended or adjusted under 35 U.S.C. 154(b) by 259 days.

(21) Appl. No.: 13/885,530

(22) PCT Filed: Nov. 9, 2011

(86) PCT No.: PCT/EP2011/069695  
§ 371 (c)(1),  
(2), (4) Date: Jun. 26, 2013

(87) PCT Pub. No.: WO2012/065886  
PCT Pub. Date: May 24, 2012

(65) Prior Publication Data  
US 2013/0319406 A1    Dec. 5, 2013

(30) Foreign Application Priority Data

Nov. 19, 2010   (DK) .................................. 2010 01052

(51) Int. Cl.  
*A61M 16/00* (2006.01)  
*A61M 16/04* (2006.01)  
*A61B 1/267* (2006.01)

(52) U.S. Cl.  
CPC .......... *A61M 16/0488* (2013.01); *A61B 1/267* (2013.01); *A61M 16/0495* (2014.02); *A61M 2205/502* (2013.01)

(58) Field of Classification Search  
CPC .......... A61B 1/267; A61M 2205/502; A61M 16/0495; A61M 16/0488; A61M 16/04; A61M 2210/0656; A61M 2210/065  
USPC ............ 128/200.24, 200.26, 207.14, 207.15; 600/120, 127, 129, 185–200  
See application file for complete search history.

(56) References Cited

U.S. PATENT DOCUMENTS

| 5,038,766 | A | | 8/1991 | Parker |
| 5,287,848 | A | | 2/1994 | Cubb et al. |
| 5,303,697 | A | | 4/1994 | Brain |
| 5,845,634 | A | * | 12/1998 | Parker ...................... 128/200.26 |
| 5,937,859 | A | | 8/1999 | Augustine et al. |

(Continued)

FOREIGN PATENT DOCUMENTS

WO    WO 2011/012677    2/2011

OTHER PUBLICATIONS

International Search Report PCT/ISA/210 for PCT/EP2011/069695 dated Jan. 23, 2012.

(Continued)

*Primary Examiner* — Bradley Philips  
*Assistant Examiner* — Victoria Leszczak  
(74) *Attorney, Agent, or Firm* — Faegre Baker Daniels LLP

(57) ABSTRACT

An intubation guide for guiding, positioning and/or insertion of e.g. an endotracheal tube in a patients trachea, and where the intubation guide comprises a relatively flexible guide extending from the distal end of a relatively stiff positioning handle having a curved section between its distal and proximal end, wherein the guide element forms a scoop shaped guide in extension of the positioning handle, and in that the positioning handle comprises an intubation channel extending along the positioning handle, and having a first end near the proximal end of the positioning handle, and the other end at the distal end near the guide scoop.

19 Claims, 3 Drawing Sheets

(56) References Cited

U.S. PATENT DOCUMENTS

| | | | |
|---|---|---|---|
| 6,070,581 A * | 6/2000 | Augustine et al. ...... 128/207.15 | |
| 6,543,447 B2 | 4/2003 | Pacey | |
| 2002/0011249 A1 | 1/2002 | Augustine et al. | |
| 2002/0117171 A1 | 8/2002 | Parker | |
| 2003/0037790 A1 | 2/2003 | Brain | |
| 2005/0268917 A1 | 12/2005 | Boedeker et al. | |
| 2007/0102001 A1 | 5/2007 | Brain | |
| 2008/0078402 A1 | 4/2008 | Mongeon | |
| 2011/0178372 A1 | 7/2011 | Pacey et al. | |
| 2011/0203594 A1 | 8/2011 | Brain | |

OTHER PUBLICATIONS

Danish Search Report dated Jun. 1, 2011 issued in corresponding Danish Priority Application No. PA 2010 01052.

International Preliminary Report on Patentability issued by the European Patent Office on Oct. 26, 2012 for related International Patent Application No. PCT/EP2011/069695; 12 pages.

* cited by examiner

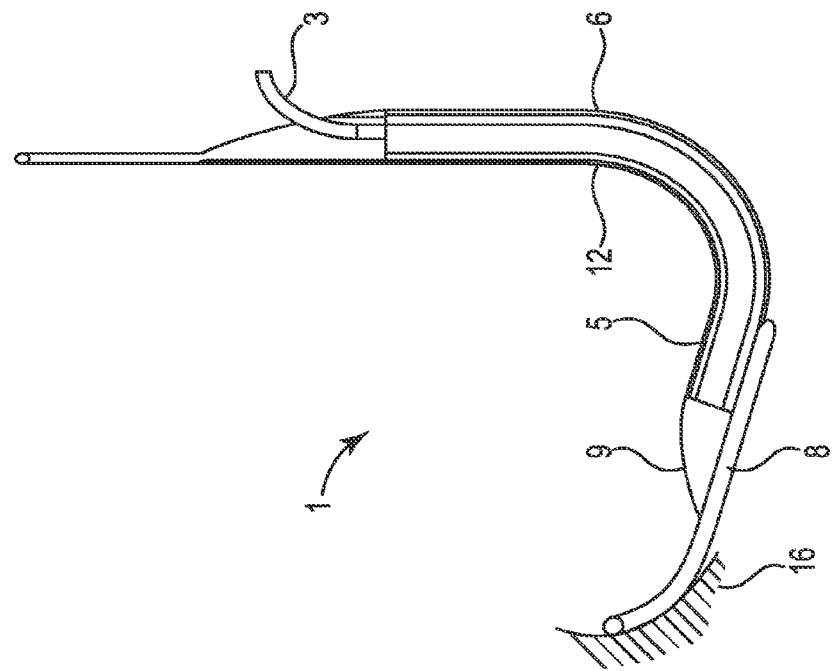
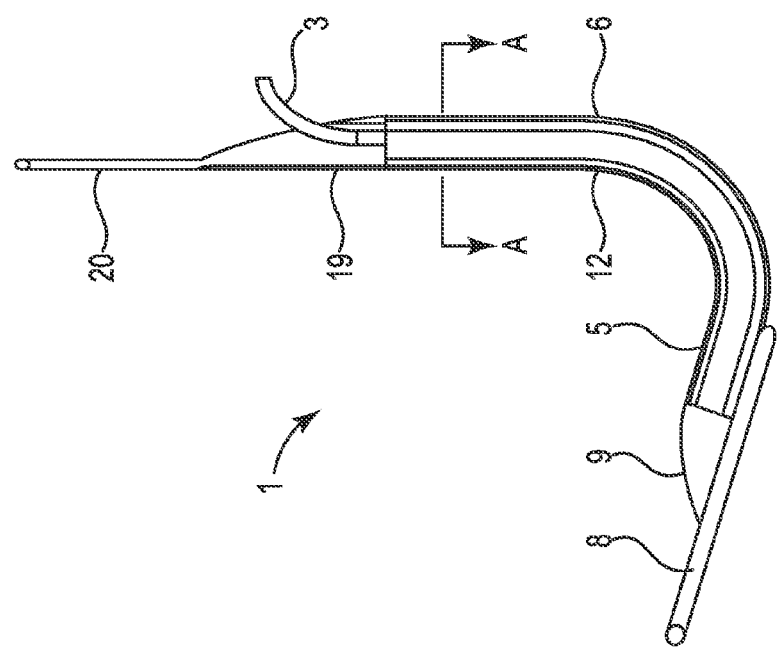

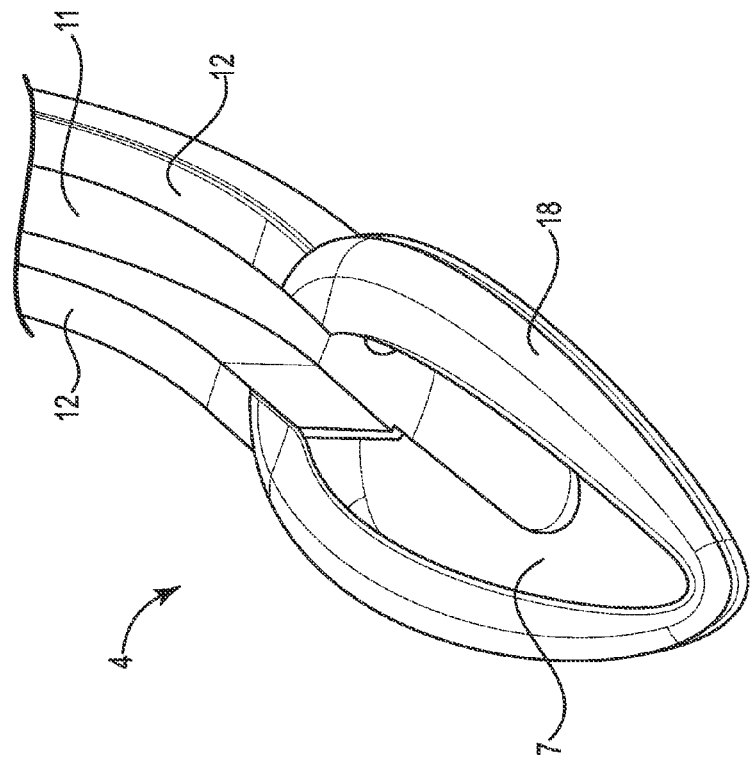
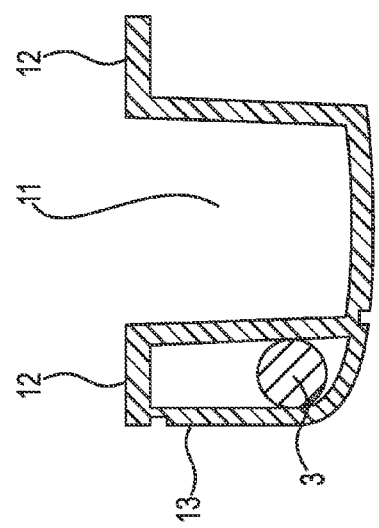
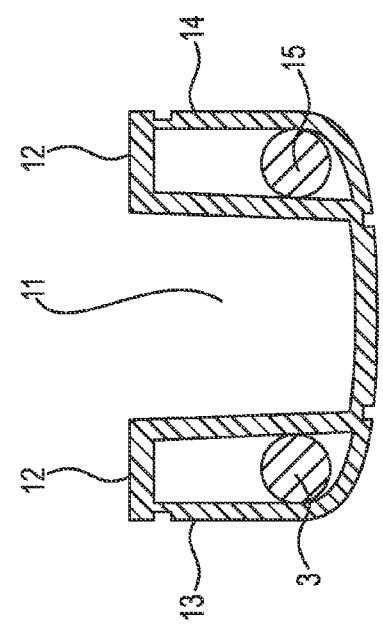
Fig. 7
Fig. 5
Fig. 6

TRACHEAL INTUBATION GUIDE

CROSS-REFERENCE TO RELATED APPLICATIONS

This application is the national phase under 35 U.S.C. §371 of PCT International Application No. PCT/EP2011/069695 which has an International filing date of Nov. 9, 2011, which designated the European Patent Office and which claims priority to Danish patent application number PA 2010-01052 filed Nov. 19, 2010.

TECHNICAL FIELD

The present invention relates to a tracheal intubation guide for guiding, positioning and insertion of e.g. an endotracheal tube in a patient's trachea, and where the intubation guide comprises a relatively flexible guide element being attached to the distal end of a relatively stiff, elongated and curved positioning handle, so that it is possible, by manipulating the proximal end of the positioning handle, to insert the guide scoop in the mouth of a patient, and to push the guide scoop down the throat of a patient, and place it in a position under the patient's epiglottis and larynx.

DESCRIPTION OF RELATED ART

Intubation guides of the above mentioned type are well known in many different embodiments. A common use for such intubation guides is to provide a guide for insertion of e.g. an endotracheal tube into the patient's trachea. In most patients insertion of an endotracheal tube may be readily performed under direct laryngoscopy of the patient's vocal cords using a conventional rigid laryngoscope to create a direct line of vision for the person performing the intubation procedure. However, it is not always easy and sometimes impossible to obtain full vision of the patient's vocal cords with the result that correct insertion of the endotracheal tube is difficult and unreliable.

U.S. Pat. No. 5,287,848 discloses one example of an intubation guide, an eyepiece arranged for visualization of the vocal cords. The structure of this intubation guide is made from a one piece, hard plastic, structure being difficult to pass gently behind the tongue and underneath the tip of the patient's epiglottis.

U.S. Pat. No. 5,038,766 discloses another example of such an intubation guide mentioned above, where the positioning handle is made of a curved blade member and the guide element is formed as a plug shaped element made from a relatively soft material, and having a central channel, so that the curved blade member can slide the guide element down the throat of the patient until the guide element engages e.g. with the patient's epiglottis and thereby resists further insertion of the guide element, when the correct position of the guide element is reached.

A recurring problem when inserting such intubation guides in a patient is that it is difficult, due to either the size of the guide element or to the hard material used for the guide tip, to insert the intubation guide without the risk of causing trauma to the patient.

SUMMARY OF THE INVENTION

The main object of the present invention is therefore to provide an intubation guide being easy to insert without risk of trauma to the patient.

This is obtained according to the present invention as defined in claim 1, and especially by having the guide element forming a scoop shaped structure as an extension of the positioning handle, and in that the positioning handle comprises an intubation channel extending along the positioning handle, and having a first end near the proximal end of the positioning handle, and the other end at the distal end near the guide scoop.

Thereby the flexible guide scoop is easier to slide along the palate, below the root of the tongue of the patient, and below the tip of the epiglottis without the risk of causing trauma to the patient, and when the guide scoop is placed correctly, then the relatively rigid positioning handle provides the possibility of easy manipulation of the distal end of the positioning handle, so that e.g. an endotracheal tube can be slid into the channel and correctly directed to the patient's trachea.

In a preferred embodiment the intubation channel is open along its entire length on one side, and at the concave side of the curved section of the positioning handle facing the patient's tongue and epiglottis when the intubation guide is inserted correctly in a patient. Thereby it is easy to remove the intubation guide after having inserted e.g. the endotracheal tube correctly.

In a preferred embodiment the flexible guide scoop forms an extension of the distal end of the positioning handle and extends at least from the convex side of the intubation channel facing away from the patient's epiglottis when the intubation guide is inserted correctly in a patient, and so that the channel end at the distal end of the positioning handle is placed on one side of the scoop facing the epiglottis when the intubation guide is inserted correctly in a patient.

In this relation the flexible scoop may preferably comprise a substantially flat and flexible plate or sheet having an outer periphery, and in that the outer periphery comprises a flexible flange, a flexible inflated or inflatable tube or another flexible means arranged and adapted for stabilizing the flexible plate or sheet.

Furthermore in a preferred embodiment the flexible scoop or the positioning handle comprises at least one wedge portion that forms an extension of the distal end of the positioning handle, and where the wedge portion has its wedge point pointing away from the positioning handle. Thereby it is easy to pass the flexible guide scoop under the patient's epiglottis, as the wedge portion engages the epiglottis and lifts the epiglottis upwardly in the throat of the patient, so that a free view of the vocal cords and an unrestricted passageway for e.g. an endotracheal tube is provided.

The intubation guide according to the invention is very suitable for video assisted guiding of e.g. an endotracheal tube. In this relation a preferred embodiment comprises a second channel extending at least partly along the positioning handle and having one end being placed close to the end of the intubation channel placed at the distal end of the positioning handle.

In this relation the second channel may preferably form a tube at least at its end closest to the distal end of the positioning handle, and having an optical window arranged for closing the end of the tube at the distal end of the positioning handle, and where the tube and the optical window be arranged such that it allows an imaging device like an endoscopic video device to be inserted into the tube, and be positioned so that it can provide images of the area on the side of the flexible scoop facing a patient's epiglottis, when the intubation guide is correctly inserted in a patient.

The positioning handle may further comprise a third channel extending at least partly along the positioning handle and having an open end being placed close to the end of the intubation channel placed at the distal end of the positioning handle. This facilitates the use of other instruments, such as e.g. a surgical instrument without obstruction of the other channels.

In a preferred embodiment the positioning handle comprises an extension from the proximal end of the positioning handle, so that easy manipulation of the positioning handle is obtained.

Due to its structural simplicity the intubation guide according to the invention is especially advantageous as a disposable unit. In this relation it is especially advantageous when the handle is made from a relatively hard plastic material, and the scoop is made from a relatively soft plastic material, and where the scoop is attached to the positioning handle by gluing, welding or moulding.

BRIEF DESCRIPTION OF THE DRAWINGS

In the following, the invention will be described in greater detail with reference to embodiments shown by the enclosed figures. It should be emphasized that the embodiments shown are used for example purposes only and should not be used to limit the scope of the invention.

FIG. 3 shows the intubation guide shown in FIG. 1 seen from one side, and with an unflexed guide scoop.

FIG. 4 shows the intubation guide shown in FIG. 1 seen from one side, and with a flexed guide scoop.

FIG. 5 shows a cross-section of one embodiment of the intubation guide according to the invention taken along the line A-A on FIG. 3.

FIG. 6 shows an alternative cross-section of a second embodiment of the intubation guide according to the invention.

FIG. 7 shows an alternative embodiment of the flexible guide scoop.

DETAILED DESCRIPTION OF THE EMBODIMENTS

Figure 2:
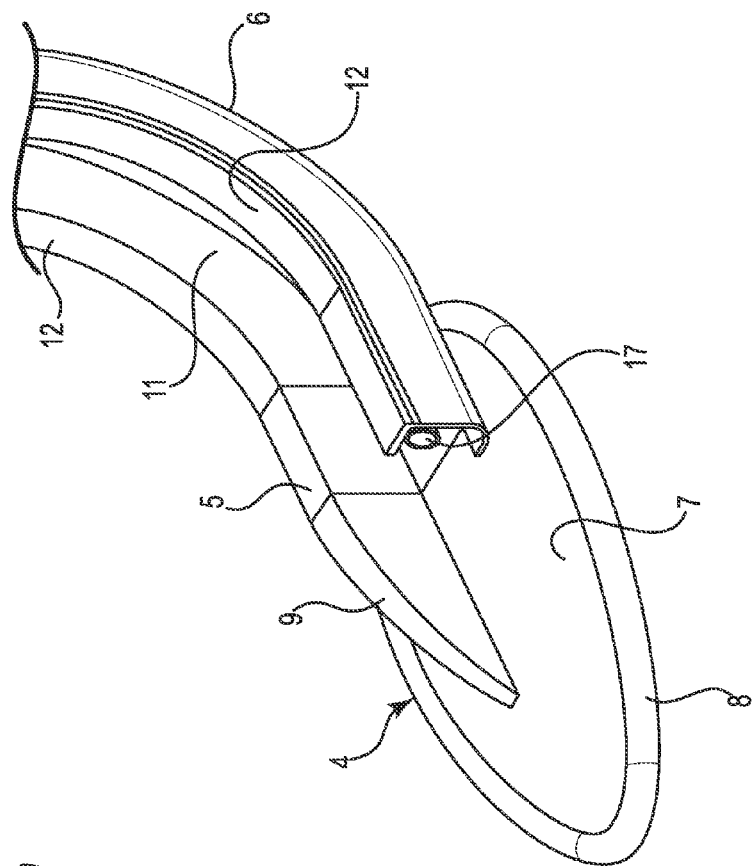
FIG. 2 is an enlarged view of the guide scoop on the intubation guide shown in FIG. 1.
Figure 1:
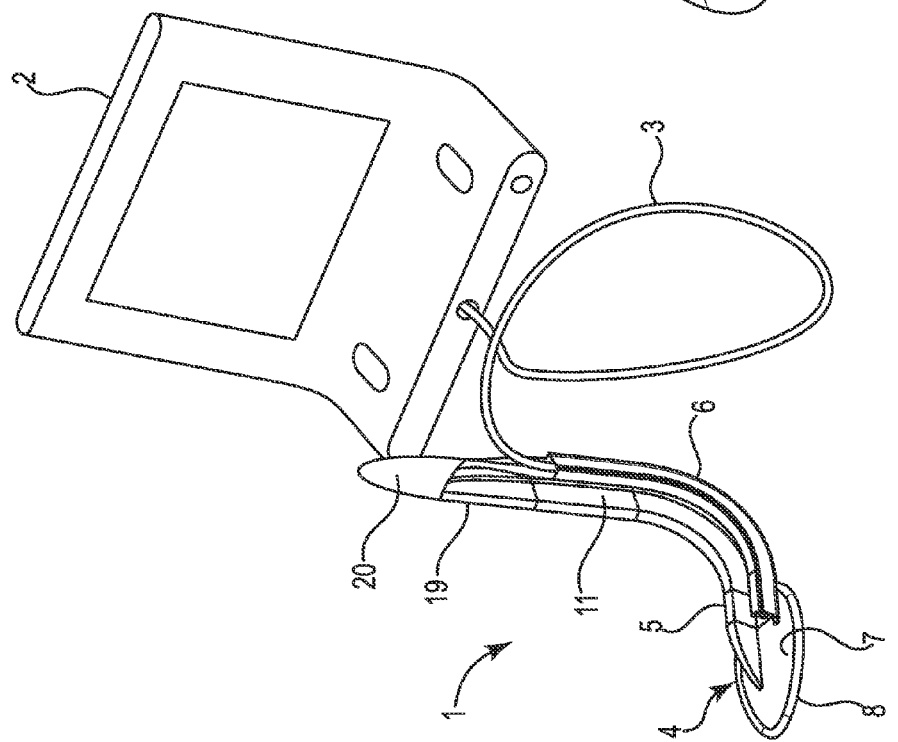
FIG. 1 shows an intubation guide according to the invention fitted with an endoscopic video device.

FIG. 1 shows one embodiment of an intubation guide 1 according to the present invention being equipped with an endoscopic video device comprising a display unit 2, and a video camera 17 being placed in the intubation guide 1 and connected to the display unit 2 via the wiring 3.

Although an intubation guide according to the invention is especially advantageous for use with endoscopic video systems it may, however, also be used without such a device.

FIGS. 2 to 5 show different details of the intubation guide according to FIG. 1. The Intubation guide 1 has a guide scoop 4 arranged on the distal end 5 on the positioning handle 6. This guide scoop is in this embodiment a flat plate or sheet 7 that is made from a flexible material, and along its periphery it is stabilized by means of an inflated tube 8, so that it forms a flexible scoop shaped structure having a size and flexibility that facilitates that the guide scoop can be inserted into the throat of a patient by flexing the guide scoop so that it easily slides e.g. along the patient's palate 16, below the root of the tongue and below the tip of the epiglottis with a minimum of risk of creating trauma to the patient. As an example FIG. 4 shows the guide scoop being flexed against the patient's palate 16 but it is evident that the flexible guide scoop is flexible in many other directions, but is able to return to its original shape due to the inflated tube 8.

For the purpose of providing easy manipulation of the intubation guide, then the proximal end 19 of the intubation guide is provided with an extension 20.

On the upper side of the guide scoop 4 is arranged a ramp forming a wedge portion 9 extending from the distal end 5 of the positioning handle 6 and forward in extension of the distal end 5. This wedge portion 9 has the function of pushing the epiglottis aside when the guide scoop 4 is slid behind or under the patient's epiglottis, so that an unrestricted passage to the patient's trachea is obtained.

The positioning handle 6 is made of a relatively hard plastic material and comprises an intubation channel 11 that serves as a conduit for insertion of e.g. an endotracheal tube (not shown), and thereby it is possible to use the positioning handle to manipulate the tracheal tube into the patient's trachea when the intubation guide is correctly inserted in a patient, by pushing the endotracheal tube in the channel to extend from the distal end 5 of the positioning handle 6, and steering the endotracheal tube into the trachea of the patient.

The intubation channel 11 is open on one side namely the concave side of the curved positioning handle 6, and this concave side will, when the intubation guide rests against the tongue, so that the tongue closes the intubation channel 11 and thereby ensures that the endotracheal tube stays in the intubation channel 11 when it is slid down via the intubation channel 11.

After having inserted the endotracheal tube into the patient, then the open side of the intubation channel 11 allows that the intubation guide 1 can be removed from the patient without substantial manipulation of the endotracheal tube.

For the purpose of avoiding that the tongue closes the channel a flange 12 is arranged on each side of the opening in the intubation channel 11.

FIG. 5 is a cross-section of the proximal end of the positioning handle 6 of the intubation guide 1, viewed from its proximal end. The cross-section is taken along line A-A shown in FIG. 3. Next to the intubation channel 11 is arranged a second channel 13 as seen especially on FIG. 5 for the insertion of a endoscopic video camera, and at the distal end of the positioning handle 6 is arranged a window for closing the end at the second channel.

FIG. 6 is a cross-sectional proximal end view of an alternative embodiment of an intubation guide according to the invention. The cross-section is taken along line A-A shown in FIG. 3 with reference to a different embodiment of the intubation guide. As shown in FIG. 6 a third channel 14 is provided, where this channel may provide the possibility of inserting other instruments 15 into the patient via the intubation guide.

It will be evident to the skilled person that the present invention may be realized in other embodiments than the one discloses in FIGS. 1 to 4. As an example of this, FIG. 7 shows another embodiment of an intubation guide, where the plate or sheet 7 is stabilized by a flange 18 instead of the inflated tube 8 according to FIGS. 1 to 4. In this embodiment the wedge 9 shown on FIGS. 1 to 4 is integrated in the flange 18 on FIG. 7.

The invention claimed is:

1. An intubation guide for positioning an endotracheal tube in a patient's trachea, the intubation guide comprising:
 a positioning handle having a proximal end, a distal end, and a curved section therebetween, the positioning handle including a wedge portion and an intubation channel open on a concave side of the curved section, the concave side of the curved section of the positioning handle facing a patient's tongue when the intubation guide is inserted correctly in the patient, the intubation channel defined by a first flange, a second flange opposite the first flange, and a connecting portion connecting the first flange to the second flange, the connecting portion having an anterior surface adapted to guide insertion of the endotracheal tube into the patient; and a guide element connected to and extending from the distal end of the positioning handle, the guide element including a flexible plate having an outer periphery and an inflated tube along the outer periphery of the plate, the flexible plate having an anterior surface that is substantially continuous with the anterior surface of the connecting portion, the wedge portion extending partially over the anterior surface of the flexible plate and configured to directly push the epiglottis of the patient aside when the guide element is slid behind or under the patient's epiglottis.

2. The intubation guide according to claim 1, wherein the wedge portion has a wedge point pointing away from the positioning handle.

3. The intubation guide according to claim 1, wherein the positioning handle comprises a second channel extending at least partly along the positioning handle and having a distal end at the distal end of the positioning handle.

4. The intubation guide according to claim 3, wherein the second channel has an optical window closing the distal end of the second channel, and wherein the second channel and the optical window are arranged to allow an imaging device to be inserted into the second channel and be positioned to provide images of an area in front of the guide element when the intubation guide is correctly inserted in a patient.

5. The intubation guide according to claim 1, wherein the positioning handle further comprises a second channel extending at least partly along the first flange and a third channel extending at least partly along the second flange and having an open end adjacent to the distal end of the positioning handle.

6. The intubation guide according to claim 1, wherein the positioning handle comprises an extension from the proximal end of the positioning handle for gripping by an operator.

7. The intubation guide according to claim 1, wherein the positioning handle is made from a hard plastic material, and the guide element is made from a soft plastic material, and where the guide element is attached to the positioning handle by gluing, welding or molding.

8. An intubation guide for positioning an endotracheal tube in a patient's trachea, where the intubation guide comprises:

a positioning handle having a proximal end, a distal end, and a curved section therebetween, the positioning handle comprising an intubation channel on a concave side thereof and a wedge portion, the intubation channel formed in part by a first flange arranged on one side of the intubation channel, a second flange arranged on an opposite side of the intubation channel, and a connecting portion connecting the first flange to the second flange, the connecting portion having an anterior surface adapted to guide insertion of the endotracheal tube into the patient, and the intubation channel extending from the proximal end to the distal end of the positioning handle and being open along its length between the first flange and the second flange; and a guide element that is flexible and is connected to the connecting portion of the positioning handle opposite the first flange and the second flange, the guide element including a flexible plate having an outer periphery and an inflated tube along the outer periphery of the flexible plate, the flexible plate having an anterior surface that is substantially continuous with the anterior surface of the connecting portion, wherein the positioning handle comprises a second channel adjacent the first flange and extending at least partly along the positioning handle, the second channel having a distal end adjacent the distal end of the positioning handle and a proximal end, and wherein the wedge portion extends partially over the anterior surface of the flexible plate and is configured to directly push the epiglottis of the patient aside when the guide element is slid behind or under the patient's epiglottis.

9. The intubation guide according to claim 8, wherein the first flange is on a patient's left-hand side when the intubation guide is inserted correctly in the patient.

10. The intubation guide according to claim 9, wherein the wedge portion extends from the second flange.

11. The intubation guide according to claim 10, wherein the second channel has an optical window enclosing the distal end of the second channel and configured to allow an imaging device to be inserted into the second channel through the proximal end of the second channel.

12. The intubation guide according to claim 11, wherein the positioning handle further comprises a third channel adjacent to the second flange.

13. The intubation guide according to claim 8, wherein the positioning handle further comprises an extension attached to the proximal end of the positioning handle for gripping by an operator.

14. The intubation guide according to claim 8, wherein the positioning handle is made from a hard plastic material, the guide element is made from a soft plastic material, and the guide element is attached to the positioning handle by gluing, welding or molding.

15. An intubation guide for positioning an endotracheal tube in a patient's trachea, the intubation guide comprising:

a positioning handle having a proximal end, a distal end, and a curved section therebetween, the positioning handle including a wedge portion and an intubation channel open on a concave side of the curved section and formed in part by a first flange arranged on one side of the intubation channel, a second flange arranged on an opposite side of the intubation channel, and a connecting portion connecting the first flange to the second flange, the connecting portion having an anterior surface adapted to guide insertion of the endotracheal tube into the patient; and a scoop shaped guide element comprising a plate having an outer periphery and a third flange extending from the first flange and the second flange and the outer periphery of the plate, wherein the plate is flexible and comprises an anterior surface that is substantially continuous with the anterior surface of the connecting portion, wherein the wedge portion extends partially over the anterior surface of the flexible plate and is configured to directly push the epiglottis of the patient aside when the scoop shaped guide element is slid behind or under the patient's epiglottis.

16. The intubation guide according to claim 15, wherein the positioning handle further comprises a second channel extending at least partly along the first flange and having a distal end coextensive with the distal end of the positioning handle.

17. The intubation guide according to claim 16, wherein the second channel has an optical window enclosing the distal end of the second channel and configured to allow an imaging device to be inserted into the second channel through a proximal end of the second channel.

18. The intubation guide according to claim 17, wherein the positioning handle further comprises a third channel adjacent to the second flange and having an open end adjacent to the distal end of the positioning handle.

19. The intubation guide according to claim 15, wherein the positioning handle is made from a hard plastic material, and the scoop shaped guide element is made from a soft plastic material, and where the scoop shaped guide element is attached to the positioning handle by gluing, welding or molding.

\* \* \* \* \*